United States Patent
Wyss et al.

(10) Patent No.: US 7,731,755 B2
(45) Date of Patent: Jun. 8, 2010

(54) POSTERIOR STABILIZED MOBILE BEARING KNEE

(75) Inventors: Joseph G. Wyss, Fort Wayne, IN (US); Travis D. Bennett, Huntington, IN (US)

(73) Assignee: DePuy Products, Inc., Warsaw, IN (US)

( * ) Notice: Subject to any disclaimer, the term of this patent is extended or adjusted under 35 U.S.C. 154(b) by 1191 days.

(21) Appl. No.: 10/866,381

(22) Filed: Jun. 11, 2004

(65) Prior Publication Data

US 2005/0278035 A1 Dec. 15, 2005

(51) Int. Cl.
*A61F 2/38* (2006.01)

(52) U.S. Cl. .................................... 623/20.27

(58) Field of Classification Search ............... 623/16.11, 623/18.11, 20.15, 20.21, 20.23, 20.24, 20.26, 623/20.27, 20.28, 20.29, 20.31–20.36
See application file for complete search history.

(56) References Cited

U.S. PATENT DOCUMENTS

| | | | | |
|---|---|---|---|---|
| 4,085,466 A | | 4/1978 | Goodfellow et al. | |
| 4,298,992 A | * | 11/1981 | Burstein et al. | 623/20.27 |
| 4,888,021 A | * | 12/1989 | Forte et al. | 623/20.19 |
| 5,007,933 A | * | 4/1991 | Sidebotham et al. | 623/20.27 |
| 5,147,405 A | * | 9/1992 | Van Zile et al. | 623/20.27 |
| 5,330,534 A | * | 7/1994 | Herrington et al. | 623/20.27 |
| 5,549,686 A | | 8/1996 | Johnson et al. | |
| 5,702,458 A | | 12/1997 | Burstein et al. | |
| 5,800,552 A | * | 9/1998 | Forte | 623/20.27 |
| 5,906,643 A | | 5/1999 | Walker | |
| 6,123,729 A | | 9/2000 | Insall et al. | |
| 6,325,828 B1 | | 12/2001 | Dennis et al. | |
| 6,402,786 B1 | | 6/2002 | Insall et al. | |
| 6,413,279 B1 | | 7/2002 | Metzger et al. | |
| 6,443,991 B1 | | 9/2002 | Running | |
| 6,797,005 B2 | * | 9/2004 | Pappas | 623/20.27 |
| 6,972,039 B2 | * | 12/2005 | Metzger et al. | 623/20.29 |
| 2004/0054416 A1 | | 3/2004 | Wyss et al. | |

FOREIGN PATENT DOCUMENTS

EP 0 724 868 A1 1/1995
FR 2 568 467 2/1986

* cited by examiner

*Primary Examiner*—Anu Ramana
(74) *Attorney, Agent, or Firm*—Barnes & Thornburg LLP

(57) ABSTRACT

A posterior stabilized mobile bearing knee prosthesis includes a femoral component, a tibial tray, and a bearing. The femoral component is configured to be implanted in a surgically prepared femur, with the tibial tray being configured for implantation in a prepared tibia. The bearing is supported on a platform of the tibial tray and rotates relative to the tray.

17 Claims, 7 Drawing Sheets

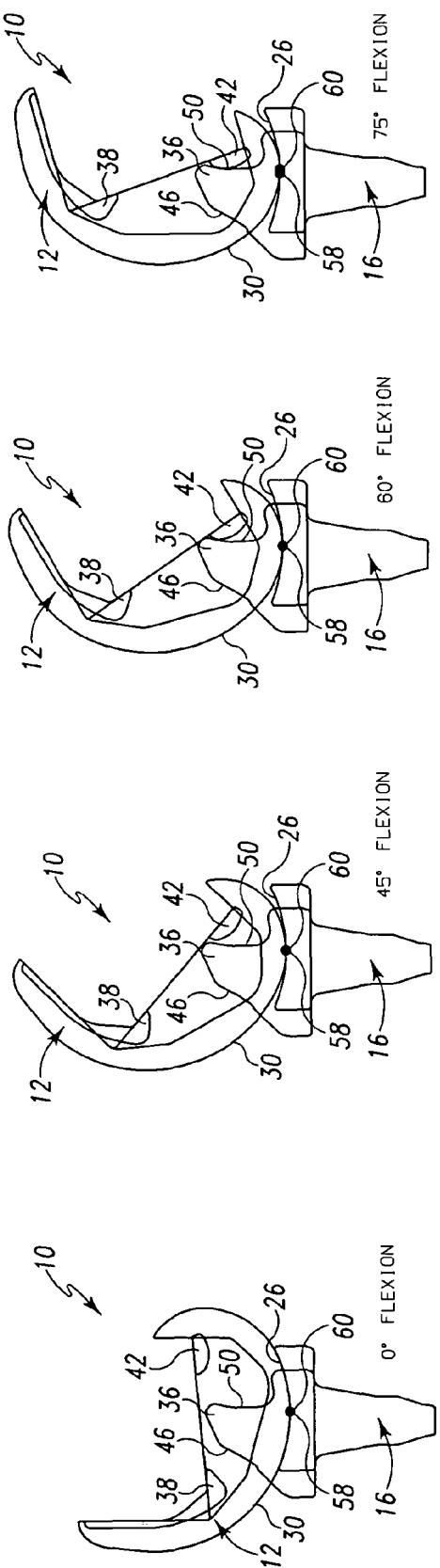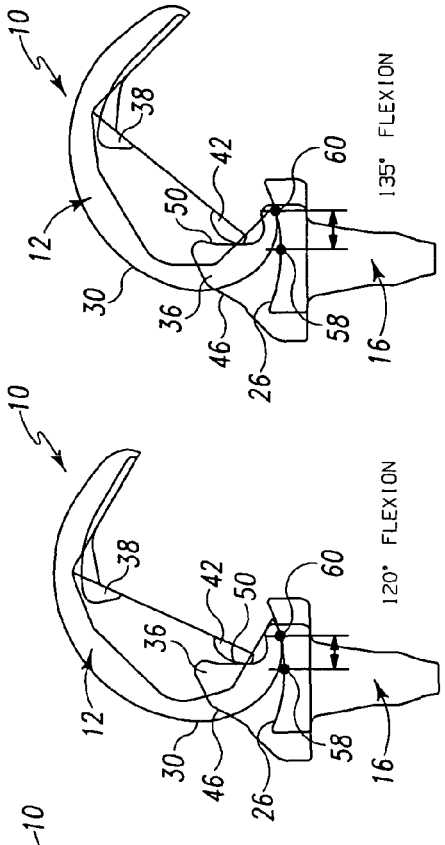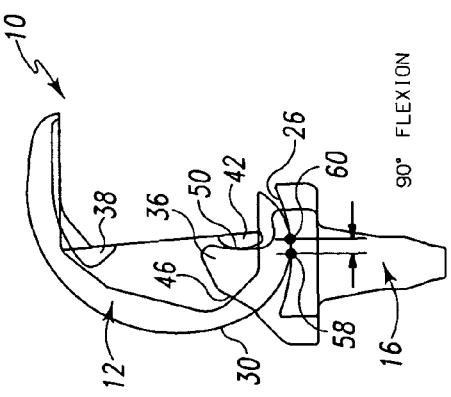

POSTERIOR STABILIZED MOBILE BEARING KNEE

FIELD OF THE DISCLOSURE

The present disclosure relates generally to an orthopaedic prosthesis, and more particularly to a knee prosthesis.

BACKGROUND

Movement (e.g., flexion and extension) of the natural human knee involves movements of the femur and the tibia. Specifically, during flexion and extension, the distal end of the femur and the proximal end of the tibia articulate relative to one another through a series of complex movements. Damage (e.g., trauma) or disease can deteriorate the bones, articular cartilage, and ligaments of the knee, which can ultimately affect the ability of the natural knee to function in such a manner. As a result, knee prostheses have been developed and implanted into surgically prepared ends of the femur and tibia.

One type of knee prosthesis is a mobile bearing knee that mimics the condylar and bearing surfaces of the knee to emulate the natural movement of the knee during flexion and extension. The tibial component of a mobile bearing knee prosthesis is configured to allow rotation about the central axis of the tibia. Moreover, certain types of mobile bearing knees, commonly referred to as posterior stabilized mobile bearing knees, include a tibial component having an upwardly projecting (i.e., superiorly projecting subsequent to implantation) spine that is positioned between the condyles of the femoral component. The spine is engaged by cam surfaces at the anterior and posterior ends of the femoral component to limit the relative anterior-posterior movement between the femur and the tibia.

SUMMARY

According to one aspect of the disclosure, a posterior stabilized mobile bearing knee prosthesis includes a femoral component, a tibial tray, and a bearing. The knee prosthesis is configured such that the bearing is positioned posteriorly of the other components during flexion and extension of the knee.

In certain illustrative embodiments, the tibial tray includes a platform having an upper surface which mates with a downwardly extending anterior surface along an anterior edge. The bearing is positioned on the platform. Throughout the range of motion of the knee, the anterior-most point of the bearing is positioned posteriorly of an imaginary line that is tangent to at least one of the medial condyle surface and the lateral condyle surface of the femoral component and intersecting a point on the anterior edge of the platform of the tibial tray.

In certain illustrative embodiments, the anterior femoral cam contacts the anterior tibial cam during hyperextension, and the femoral component rolls anteriorly relative to the bearing during hyperextension beyond contact of the anterior tibial cam and the anterior femoral cam.

The femoral component may roll anteriorly relative to the bearing through up to 18°-25° of hyperextension. The anterior femoral cam may contact the anterior tibial cam at about 13° of hyperextension.

The anterior femoral cam may contact the anterior tibial cam at about 6° of hyperextension when the tibial tray is implanted at a posterior inclination of 7°. Moreover, the femoral component may anteriorly roll relative to the bearing throughout a range of about 11°-18° of hyperextension when the tibial tray is implanted at a posterior inclination of 7°.

The above and other features of the present disclosure will become apparent from the following description and the attached drawings.

BRIEF DESCRIPTION OF THE DRAWINGS

The detailed description particularly refers to the accompanying figures in which:

FIGS. 12-19 are diagrammatic side elevational views of the knee prosthesis of FIG. 1 showing the prosthesis in various positions during flexion of the knee.

DETAILED DESCRIPTION OF THE DRAWINGS

Figure 1:
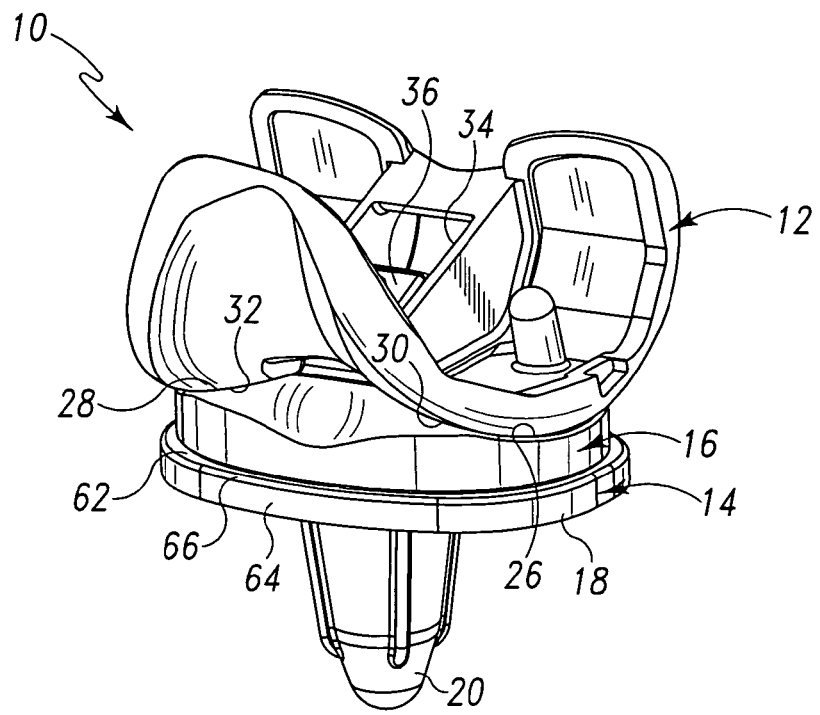
FIG. 1 is a perspective view of a posterior stabilized mobile bearing knee prosthesis.
Figure 2:
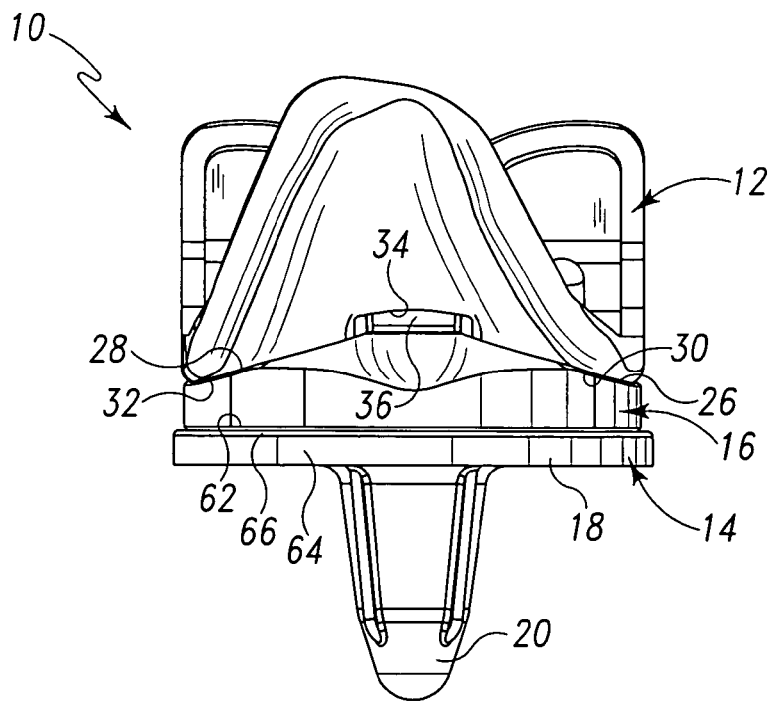
FIG. 2 is a front elevation view of the knee prosthesis of FIG. 1.
Figure 3:
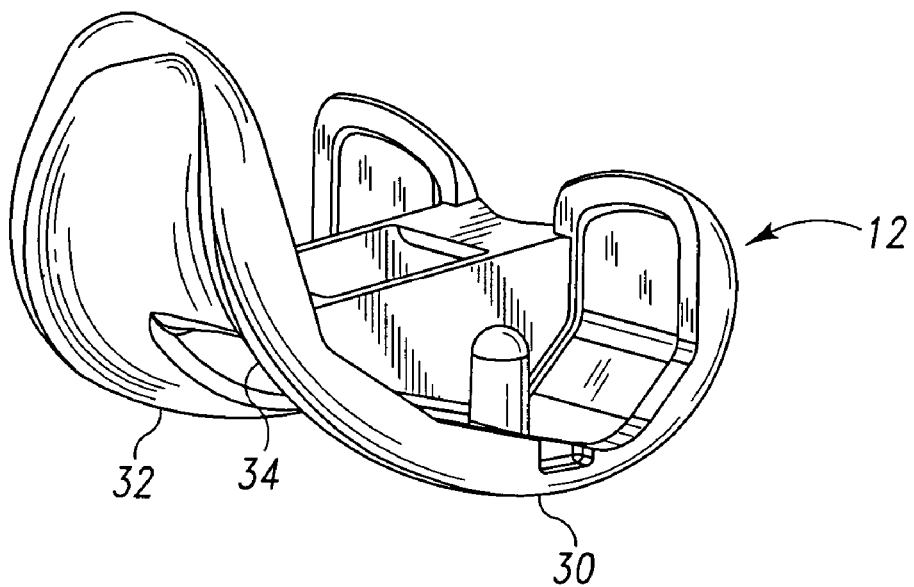
FIG. 3 is a perspective view of the femoral component of the knee prosthesis of FIG. 1.
Figure 4:
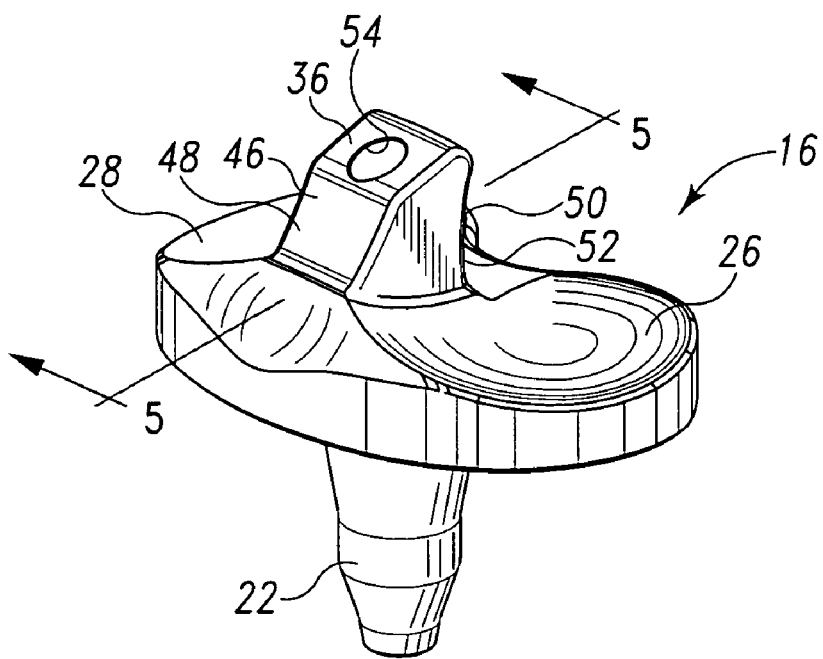
FIG. 4 is a perspective view of the bearing of the knee prosthesis of FIG. 1.
Figure 20:
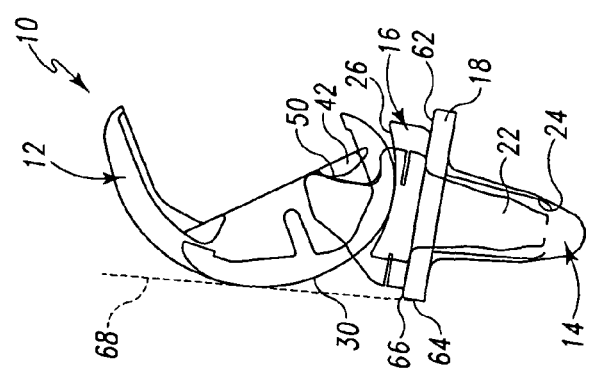
FIGS. 20-23 are diagrammatic side elevational views of the knee prosthesis of FIG. 1 showing the position of the bearing relative to the femoral component and the tibial tray.
Figure 21:
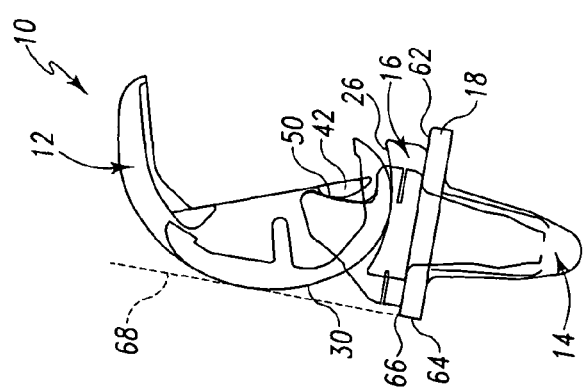
Figure 22:
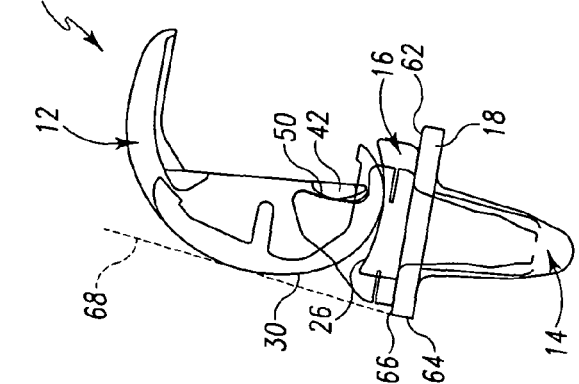
Figure 23:
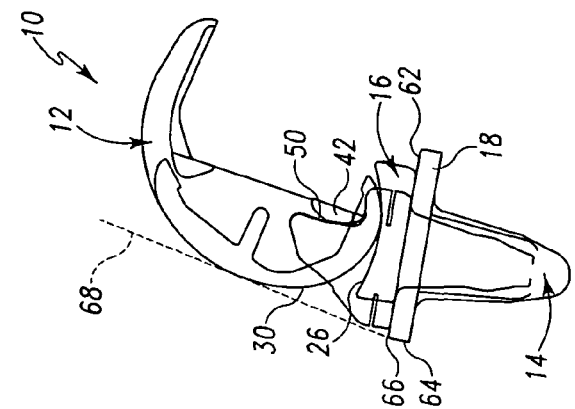

Referring now to FIGS. 1 and 2, there is shown a posterior stabilized mobile bearing knee prosthesis 10. The knee prosthesis 10 includes a femoral component 12, a tibial tray 14, and a bearing 16. The tibial tray 14 includes a platform 18 from which a stem 20 extends. The tibial stem 20 is configured to be implanted into a prepared end of the patient's tibia (not shown). The bearing 16 includes a stem 22 (see FIG. 4) that is positionable within a complementary bore 24 (see FIG. 20) in the tibial tray 14. In such a way, the bearing 16 is rotatable relative to the tibial tray 14.

The bearing 16 includes a lateral bearing surface 26 and a medial bearing surface 28. The bearing surfaces 26, 28 are configured to articulate with a lateral condyle surface 30 and a medial condyle surface 32, respectively, of the femoral component 12. Specifically, the femoral component 12 is configured to be implanted into a prepared end of the patient's femur (not shown), and is configured to emulate the configuration of the patient's natural femoral condyles. As such, the lateral condyle surface 30 and the medial condyle surface 32 are configured (e.g., curved) in a manner which mimics the condyles of a natural femur. The lateral condyle surface 30 and the medial condyle surface 32 are spaced apart from one another thereby defining an intercondylar notch 34 therebetween.

The components of the knee prosthesis that engage the natural bone, such as the femoral component 12 and the tibial tray 14, may be constructed with a biocompatible metal, such as cobalt chrome alloy. The bone engaging surfaces of these components may be textured to facilitate cementing the component to the bone. Such surfaces may also be porous coated to promote bone ingrowth for permanent fixation.

Figure 5:
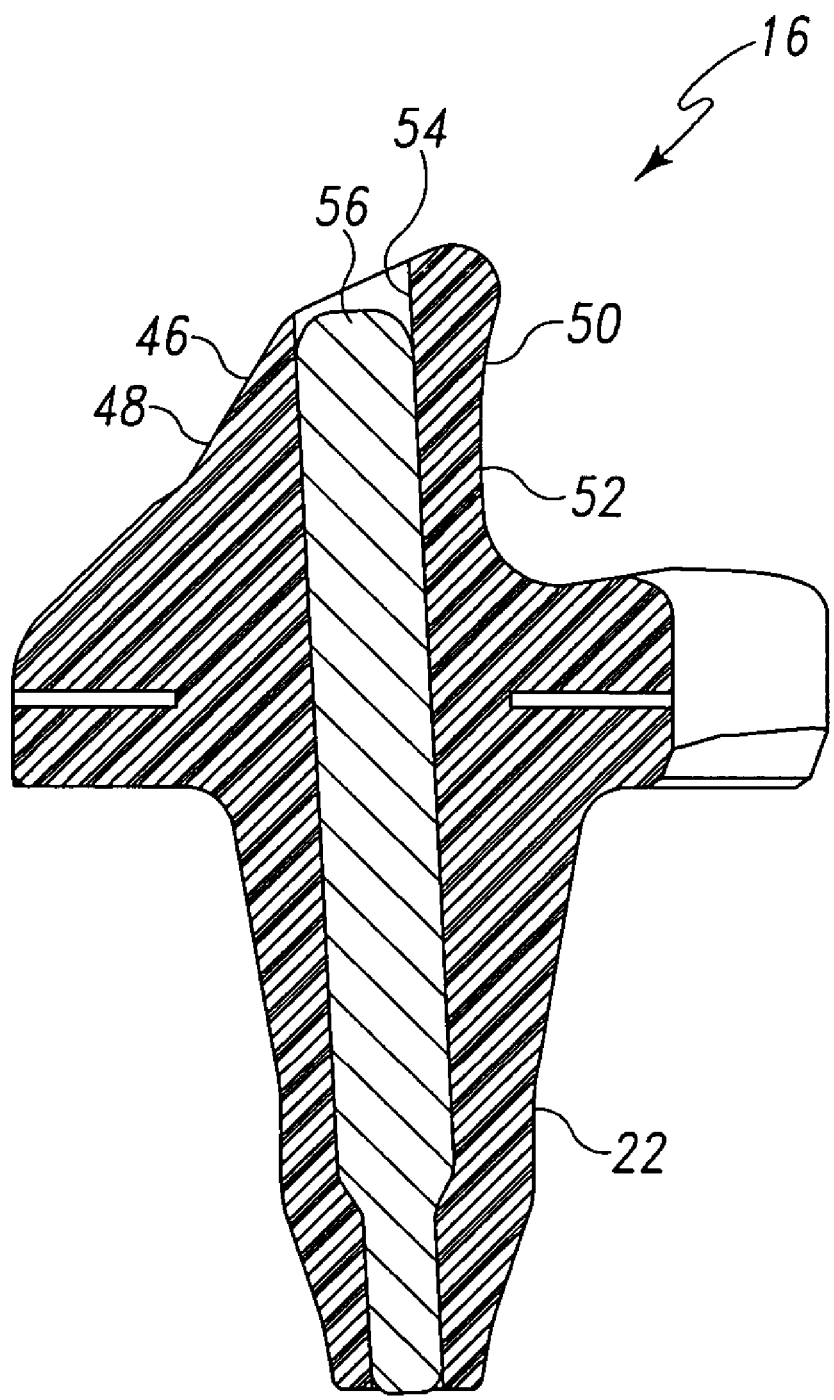
FIG. 5 is a cross sectional view of the bearing taken along the line 5-5 of FIG. 4.
Figure 9:
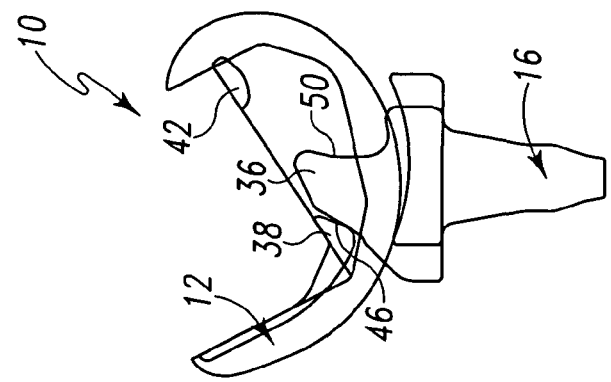
FIGS. 6-9 are diagrammatic side elevational views of the knee prosthesis of FIG. 1 showing the prosthesis in various positions during hyperextension of the knee.
Figure 8:
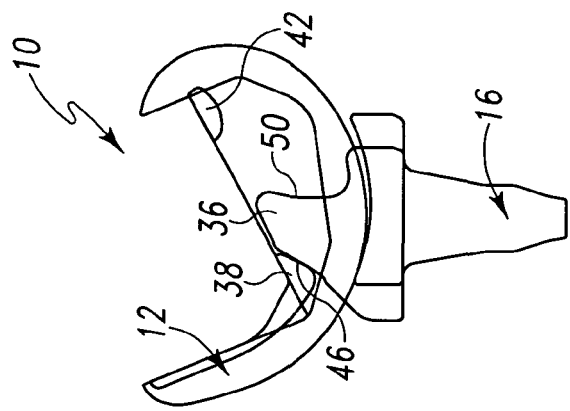
Figure 7:
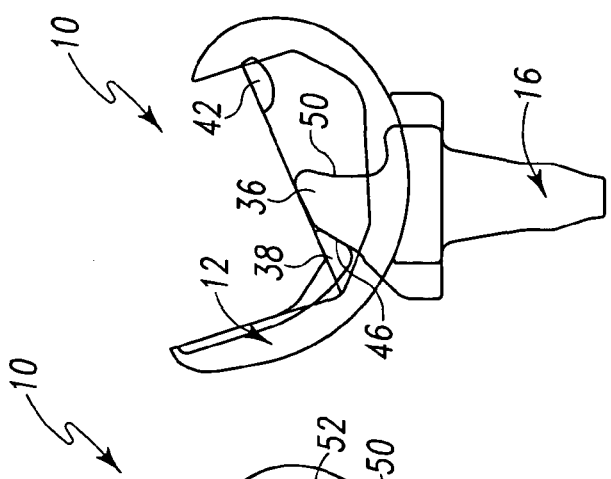

The bearing 16 may be constructed with a material that allows for smooth articulation and rotation between the bearing 16 and the other components. One such material is ultra-high molecular weight polyethylene (UHMWPE). Moreover, as shown in FIG. 5, the stem 22 of the bearing 16 has a central bore 54 extending, at least partially, therethrough. A stiffening pin 56 may be press fit or otherwise inserted into the bore 54. The pin 56 may be constructed with a metal such as a cobalt chrome alloy.

Figure 6:
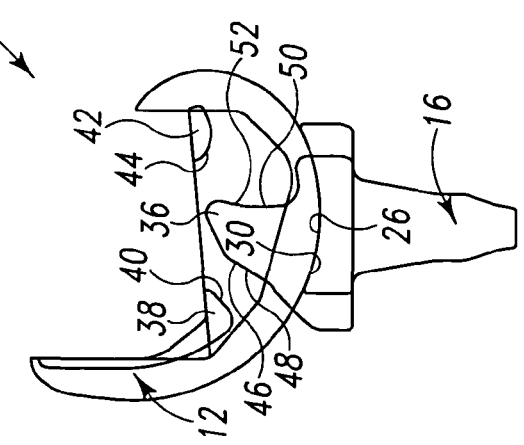

The bearing 16 includes a spine 36 that extends from the upper surface thereof. The spine 36 extends into the notch 34 of the femoral component 12. The femoral component 12 includes an anterior cam 38 having a cam face 40 and a posterior cam 42 having a cam face 44 (see FIG. 6). In a similar manner, the spine 36 has an anterior cam 46 having a cam face 48 and a posterior cam 50 having a cam face 52 (see FIGS. 4 and 6).

Figure 10:
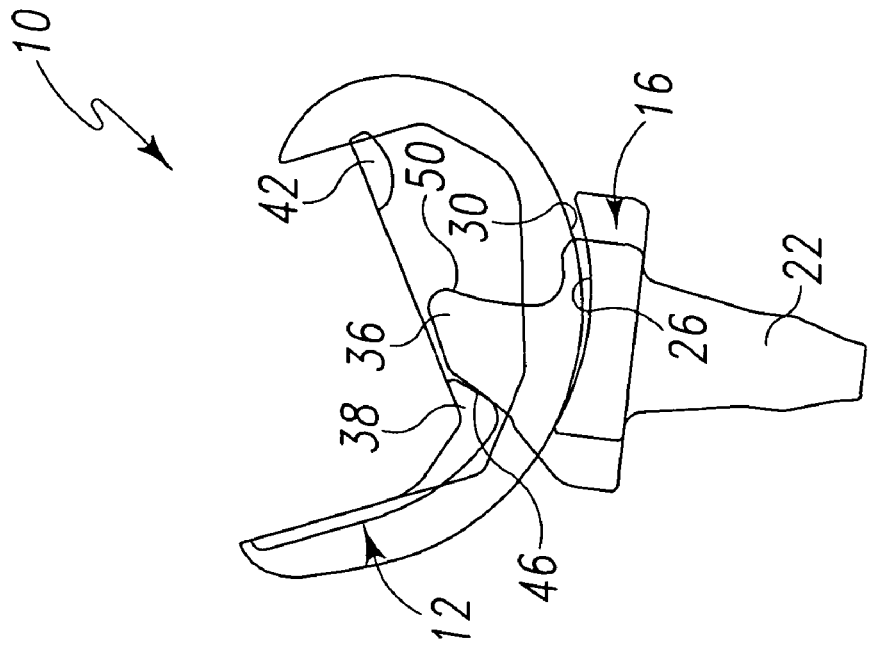
FIGS. 10 and 11 are views similar to FIGS. 6-9, but showing the prosthesis in various positions during hyperextension of the knee when the tibial tray is implanted at 7° of posterior inclination.
Figure 11:
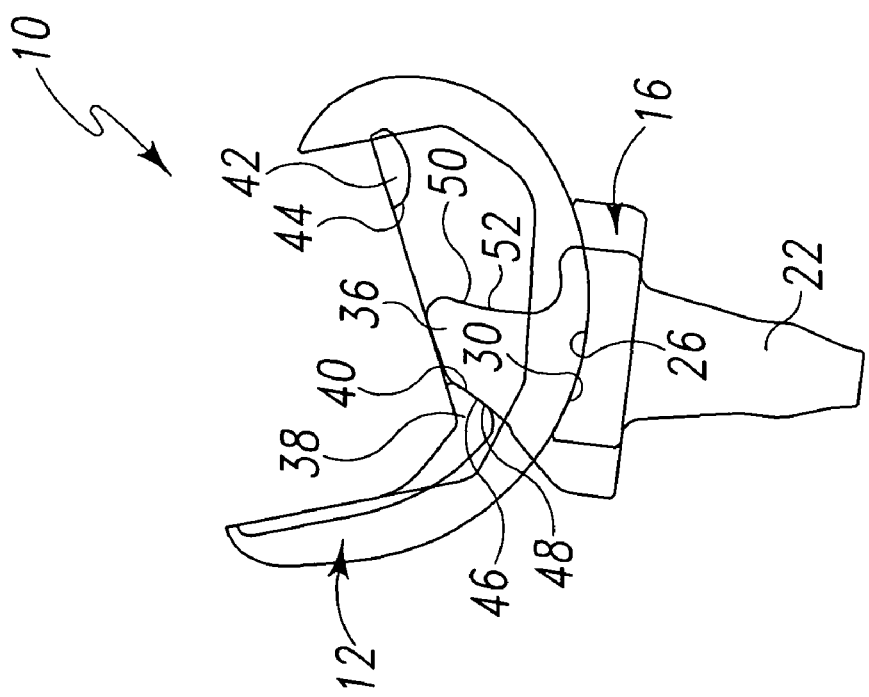

The anterior cam 38 of the femoral component 12 and the anterior cam 46 of the spine 36 are configured to engage one another at between 3° and 6° of hyperextension (depending on the posterior inclination of the tibial tray 14). In the exemplary embodiment described herein, the tibial tray 14 may be implanted at a 7° posterior inclination, as shown in FIGS. 10 and 11. In this exemplary embodiment, the anterior cam 38 of the femoral component 12 engages the anterior cam 46 of the spine 36 at about 6° of hyperextension. It should be appreciated that the anterior cam 38 of the femoral component 12 engages the anterior cam 46 of the spine 36 at different degrees of hyperextension based on the angle of posterior inclination of the tibial tray 14 (and hence the bearing 16). For example, the cams 38, 46 will engage one another at 3° of hyperextension when the tibial tray 14 (and hence the bearing 16) is implanted at a 10° posterior inclination, or at 13° of hyperextension when the tibial tray 14 (and hence the bearing 16) is implanted at a 0° posterior inclination (see, e.g., FIGS. 6-9).

Moreover, the anterior cam 38 of the femoral component 12 and the anterior cam 46 of the spine 36 are configured to cause the femoral component 12 to roll anteriorly relative to the bearing 16 at ranges of hyperextension beyond when the cams 38, 46 contact one another. In particular, the cam faces of the anterior cams 38, 46 are configured such that rolling contact exists between the femoral component 12 and the bearing 16 during hyperextension of the knee prosthesis 10 beyond initial contact of the cams 38, 46 to a point where the patient's soft tissues prevent further hyperextension of the prosthesis 10. Depending on the angle of inclination of the tibial tray 14 (and hence the bearing 16), along with the anatomy and/or condition of the patient's soft tissue, the femoral component 14 may roll anteriorly relative to the bearing 16 through a fairly wide range of hyperextension. For example, the femoral component 14 may roll anteriorly relative to the bearing 16 through up to 18°-25° of hyperextension when the tibial tray 14 is implanted at a 0° posterior inclination (see, e.g., FIGS. 6-9). As shown in FIGS. 10 and 11, when the tibial tray 14 is implanted at a 7° posterior inclination, the patient's soft tissues will typically prevent further hyperextension of the prosthesis 10 than from about 11° to about 18° of hyperextension (and perhaps less depending on the particular anatomy and/or condition of the patient's soft tissue).

The posterior cam 42 of the femoral component 12 and the posterior cam 50 of the spine 36 cooperate to provide posterior roll-back during flexion of the knee. As shown in FIGS. 12-19, in the exemplary embodiment described herein, the posterior femoral cam 42 engages the posterior tibial cam 50 at about 50° of flexion. At that point, the posterior tibial cam 50 prevents further anterior translation of the femoral component 12. As such, from 50° of flexion to about 120° of flexion (and beyond), the posterior femoral cam 42 engages the posterior tibial cam 50 and roll-back occurs.

As shown in FIGS. 12-19, in the exemplary embodiment of the knee prosthesis 10 described herein, from 0° to about 50° of flexion, the femoral condyle surfaces 30, 32 articulate within a range of about +/−1 mm of the lowest point, i.e., the dwell point 58, of the bearing surfaces 26, 28 of the bearing 16. The dwell point 58 of the bearing 16 is relatively centrally located with the bearing surfaces 26, 28. In the exemplary embodiment described herein, the dwell point 58 is located within +/−5% of the middle of the arc length of the bearing surfaces 26, 28.

At about 50° of flexion, the posterior femoral cam 42 engages the posterior tibial cam 50 thereby preventing anterior slide of the femoral component 12. From this point through about 75° of flexion, the configuration of the cams 42, 50 allow the femoral component to roll back while articulating within the range of about +/−1 mm of the dwell point 58. At about 75° of flexion, the configuration of the cams 42, 50 forces the femoral component 12 to roll posterior on the bearing 16.

As shown in FIG. 16, in the exemplary embodiment described herein, at 90° of flexion the contact point 60 of the condyle surfaces 30, 32 translates about 2 mm posteriorly from the dwell point 58. At 105° of femoral flexion, the contact point 60 of the condyle surfaces 30, 32 translates about 3 mm posteriorly from the dwell point 58 (see FIG. 17). As shown in FIG. 18, at 120° of femoral flexion, the contact point 60 of the condyle surfaces 30, 32 translates about 5 mm posteriorly from the dwell point 58. At 135° of femoral flexion, the contact point 60 of the condyle surfaces 30, 32 translates about 7 mm posteriorly from the dwell point 58 (see FIG. 19).

It should be appreciated that the above described kinematics of the knee prosthesis 10 are exemplary in nature with other configurations being contemplated. For example, although described as occurring at 50° of flexion, initial contact between the cams 42, 50 may occur at any point from about 40° to about 60° of flexion. Moreover, roll in flexion may occur at any point from about 70° to about 90° of flexion.

In addition, the distance the contact point 60 translates posteriorly from the dwell point 58 may also be varied from the exemplary values described above. For example, at about 90° of flexion, the contact point 60 may translate from about 1 mm to about 2.5 mm posterior of the dwell point 58. Moreover, at about 105° of flexion, the contact point 60 may translate from about 2 mm to about 3.5 mm posterior of the dwell point 58. Further, at about 120° of flexion, the contact point 60 may translate from about 3 mm to about 5 mm posterior of the dwell point 58. At about 135° of flexion, the contact point 60 may translate from about 4 mm to about 7.5 mm posterior of the dwell point 58.

As shown in FIG. 1, the platform 18 of the tibial tray 14 has an upper surface 62 (upon which the bearing 16 is supported) which mates with a downwardly extending anterior surface 64 along and anterior edge 66. As shown in FIGS. 20-23, at any position throughout the range of motion of the knee prosthesis 10, an imaginary line 68 may be drawn which is tangent to the lateral condyle surface 30 and intersects the anterior edge 66 of the platform 18 of the tibial tray 14. At any position throughout the range of motion of the knee prosthesis 10, an imaginary line 68 may also be drawn which is tangent to the medial condyle surface 32 and intersects the anterior edge 66 of the platform 18 of the tibial tray 14. When viewed from the side elevational views of FIGS. 20-23, both imaginary lines 68 appear as a single line.

Throughout the range of motion of the knee prosthesis 10, the bearing 16 is positioned posteriorly of the other components of the prosthesis. Specifically, the anterior-most aspect of the bearing 16 is positioned posteriorly of the imaginary lines 68 throughout movement of the knee prosthesis 10. As such, when viewed in the side elevational views of FIGS. 20-23, no portion of the bearing 16 intersects the imaginary lines 68 throughout the range of motion of the knee prosthesis 10. For example, at 120° of flexion (see FIG. 23), the anterior-most point of the bearing 16 is positioned posteriorly of the imaginary lines 68. Such a configuration reduces, or even prevents, contact of the bearing 16 with the surrounding soft tissue thereby potentially reducing occurrences of hemoarthrosis.

While the disclosure is susceptible to various modifications and alternative forms, specific exemplary embodiments thereof have been shown by way of example in the drawings and has herein be described in detail. It should be understood, however, that there is no intent to limit the disclosure to the particular forms disclosed, but on the contrary, the intention is to cover all modifications, equivalents, and alternatives falling within the spirit and scope of the invention as defined by the appended claims.

There are a plurality of advantages of the present disclosure arising from the various features of the apparatus and methods described herein. It will be noted that alternative embodiments of the apparatus and methods of the present disclosure may not include all of the features described yet still benefit from at least some of the advantages of such features. Those of ordinary skill in the art may readily devise their own implementations of an apparatus and method that incorporate one or more of the features of the present disclosure and fall within the spirit and scope of the present disclosure.

The invention claimed is:

1. A posterior stabilized mobile bearing knee prosthesis, comprising:
a femoral component having a medial condyle surface and a lateral condyle surface,
a tibial tray having a platform with an elongated stem extending therefrom, the platform has an upper surface which mates with a downwardly extending anterior surface along an anterior edge, and
a bearing positioned on the platform, the bearing having (i) a medial bearing surface configured to articulate with the medial condyle surface of the femoral component, (ii) a lateral bearing surface configured to articulate with the lateral condyle surface of the femoral component, (iii) a stem integrally formed with the bearing, the stem being received within a complementary bore in the tibial tray, and (iv) a spine integrally formed with the bearing, the spine being received within a notch in the femoral component,
wherein the spine of the bearing contacts the femoral component such that at 120° of flexion, when viewed in a side elevational view, the anterior-most point of the bearing is positioned posteriorly of an imaginary line that is tangent to at least one of the medial condyle surface and the lateral condyle surface of the femoral component and intersecting a point on the anterior edge of the platform of the tibial tray.

2. The knee prosthesis of claim 1, wherein the imaginary line is tangent to the medial condyle surface at the anterior-most point of the medial condyle surface.

3. The knee prosthesis of claim 1, wherein the imaginary line is tangent to the lateral condyle surface at the anterior-most point of the lateral condyle surface.

4. The knee prosthesis of claim 1, wherein at 120° of flexion:
the medial condyle surface articulates on the medial bearing surface within a range of 3 mm-5 mm posterior to the dwell point of the medial bearing surface, and
the lateral condyle surface articulates on the lateral bearing surface within a range of 3 mm-5 mm posterior to the dwell point of the lateral bearing surface.

5. The knee prosthesis of claim 1, wherein at 120° of flexion:
the medial condyle surface articulates on the medial bearing surface at a point that is approximately 5 mm posterior to the dwell point of the medial bearing surface, and
the lateral condyle surface articulates on the lateral bearing surface at point that is approximately 5 mm posterior to the dwell point of the lateral bearing surface.

6. A posterior stabilized mobile bearing knee prosthesis, comprising:
a femoral component having a medial condyle surface and a lateral condyle surface,
a tibial tray having a platform with an elongated stem extending therefrom, the platform has an upper surface which mates with a downwardly extending anterior surface along an anterior edge, and
a bearing positioned on the platform, the bearing having (i) a medial bearing surface configured to articulate with the medial condyle surface of the femoral component, (ii) a lateral bearing surface configured to articulate with the lateral condyle surface of the femoral component, (iii) a stem integrally formed with the bearing, the stem being received within a complementary bore in the tibial tray, and (iv) a spine integrally formed with the bearing, the spine being received within a notch in the femoral component,
wherein the spine of the bearing contacts the femoral component such that at any position throughout the range of motion of the knee prosthesis, when viewed in a side elevational view, the anterior-most point of the bearing is positioned posteriorly of an imaginary line that is tangent to at least one of the medial condyle surface and the lateral condyle surface of the femoral component and intersecting a point on the anterior edge of the platform of the tibial tray.

7. The knee prosthesis of claim 6, wherein the imaginary line is tangent to the medial condyle surface at the anterior-most point of the medial condyle surface.

8. The knee prosthesis of claim 6, wherein the imaginary line is tangent to the lateral condyle surface at the anterior-most point of the lateral condyle surface.

9. The knee prosthesis of claim 6, wherein from 0°-50° of flexion:
the medial condyle surface articulates on the medial bearing surface within a range of +/−1 mm of the dwell point of the medial bearing surface, and
the lateral condyle surface articulates on the lateral bearing surface within a range of +/−1 mm of the dwell point of the lateral bearing surface.

10. The knee prosthesis of claim 6, wherein from 0°-75° of flexion:
the medial condyle surface articulates on the medial bearing surface within a range of +/−1 mm of the dwell point of the medial bearing surface, and
the lateral condyle surface articulates on the lateral bearing surface within a range of +/−1 mm of the dwell point of the lateral bearing surface.

11. The knee prosthesis of claim 6, wherein from 75°-120° of flexion:

the medial condyle surface articulates on the medial bearing surface within a range of 1 mm-5 mm posterior to the dwell point of the medial bearing surface, and the lateral condyle surface articulates on the lateral bearing surface within a range of 1 mm-5 mm posterior to the dwell point of the lateral bearing surface.

12. A posterior stabilized mobile bearing knee prosthesis, comprising:

a femoral component having (i) a pair of condyle surfaces spaced apart to define a notch therebetween, (ii) an anterior femoral cam positioned in the notch, and (iii) a posterior cam positioned in the notch, a tibial tray having a platform with an elongated stem extending therefrom, and a bearing positioned on the platform, the bearing having (i) a pair of bearing surfaces configured to articulate with condyle surfaces of the femoral component, and (ii) a spine extending integrally formed with the bearing and upwardly into the notch, the spine having an anterior tibial cam, wherein the anterior femoral cam and the anterior tibial cam are configured such that the anterior femoral cam contacts the anterior tibial cam at and beyond a predetermined degree of hyperextension, so as to cause the femoral component to roll anteriorly relative to the bearing during hyperextension beyond the predetermined degree of hyperextension.

13. The knee prosthesis of claim 12, wherein the femoral component rolls anteriorly relative to the bearing through up to 18°-25° of hyperextension.

14. The knee prosthesis of claim 12, wherein the anterior femoral cam contacts the anterior tibial cam at about 13° of hyperextension.

15. The knee prosthesis of claim 12, wherein the anterior femoral cam contacts the anterior tibial cam at about 6° of hyperextension when the tibial tray has a posterior inclination of 7°.

16. The knee prosthesis of claim 12, wherein the femoral component anteriorly rolls relative to the bearing throughout a range of about 11°-18° of hyperextension when the tibial tray has a posterior inclination of 7°.

17. A posterior stabilized mobile bearing knee prosthesis, comprising:

a femoral component having a pair of condyle surfaces spaced apart to define a notch therebetween, an anterior femoral cam is positioned in the notch, a tibial tray having a platform with an elongated stem extending therefrom, and a bearing positioned on the platform, the bearing having (i) a pair of bearing surfaces configured to articulate with condyle surfaces of the femoral component, and (ii) a spine extending integrally formed with the bearing and upwardly into the notch, the spine having an anterior tibial cam, wherein when the tibial tray has a posterior inclination of 7° (i) the anterior femoral cam engages the anterior tibial cam at about 6° of hyperextension, and (ii) the anterior femoral cam engages the anterior tibial cam such that the femoral component anteriorly rolls relative to the bearing throughout a range of about 11°-18° of hyperextension.

* * * * *